(12) United States Patent
Tichy et al.

(10) Patent No.: US 7,534,756 B2
(45) Date of Patent: May 19, 2009

(54) DEVICES, SYSTEMS, AND METHODS FOR DISPENSING DISINFECTANT SOLUTIONS COMPRISING A PEROXYGEN AND TRANSITION METAL

(75) Inventors: Daryl J. Tichy, Orem, UT (US); Brian G. Larson, Alpine, UT (US)

(73) Assignee: Solutions BioMed, LLC, Orem, UT (US)

( * ) Notice: Subject to any disclaimer, the term of this patent is extended or adjusted under 35 U.S.C. 154(b) by 0 days.

(21) Appl. No.: 11/788,742

(22) Filed: Apr. 20, 2007

(65) Prior Publication Data
US 2008/0000931 A1    Jan. 3, 2008

Related U.S. Application Data (63) Continuation-in-part of application No. 11/514,721, filed on Aug. 31, 2006, now Pat. No. 7,473,675, which is a continuation-in-part of application No. 11/361,841, filed on Feb. 24, 2006, now Pat. No. 7,462,590, which is a continuation-in-part of application No. 11/361,837, filed on Feb. 24, 2006, which is a continuation-in-part of application No. 11/361,836, filed on Feb. 24, 2006, which is a continuation-in-part of application No. 11/361,665, filed on Feb. 24, 2006, now Pat. No. 7,351,684.

(60) Provisional application No. 60/656,723, filed on Feb. 25, 2005.

(51) Int. Cl.
*C11D 7/18* (2006.01)
*C11D 3/48* (2006.01)

(52) U.S. Cl. ............. 510/372; 510/161; 510/199; 510/235; 510/238; 510/302; 510/309; 510/319; 510/362; 510/367; 510/370; 510/375; 510/382

(58) Field of Classification Search ............... 510/372, 510/161, 199, 235, 238, 302, 309, 319, 362, 510/370, 367, 375, 382
See application file for complete search history.

(56) References Cited

U.S. PATENT DOCUMENTS 716,077 A    12/1902    Morrin (Continued)

FOREIGN PATENT DOCUMENTS

GB    2189394    10/1987

(Continued)

OTHER PUBLICATIONS

U.S. Appl. No. 11/891,316, Tichy et al. filed Aug. 8, 2007.

(Continued)

*Primary Examiner*—Charles I Boyer
(74) *Attorney, Agent, or Firm*—Thorpe North & Western LLP (57) ABSTRACT

The present invention is drawn to dispensing devices and systems which can be used to store and/or dispense a disinfectant solution. The device can include a first compartment and a second compartment. The first compartment can include a first liquid composition, which includes a transition metal or alloy thereof. The second compartment is separated from the first compartment and can contain a second liquid composition that includes a peroxygen. The first and second liquid compositions are formulated to be combined so as to yield a resultant disinfectant solution. The disinfectant solution can be used to disinfect a variety of surfaces and even liquid compositions.

94 Claims, 1 Drawing Sheet

U.S. PATENT DOCUMENTS

| | | | |
|---|---|---|---|
| 734,467 | A | 7/1903 | Martien |
| 2,103,999 | A | 12/1937 | Muller et al. |
| 2,304,104 | A | 12/1942 | Klabunde et al. |
| 4,021,338 | A | 5/1977 | Harkin |
| 4,297,298 | A | 10/1981 | Crommelynch et al. |
| 4,311,598 | A | 1/1982 | Verachtert |
| 4,321,255 | A | 3/1982 | Boden |
| 4,414,127 | A * | 11/1983 | Fu .............................. 510/115 |
| 4,655,975 | A | 4/1987 | Snoble |
| 4,826,658 | A | 5/1989 | Kay |
| 4,915,955 | A | 4/1990 | Gomori |
| 5,349,083 | A | 9/1994 | Brougham et al. |
| 5,357,636 | A * | 10/1994 | Dresdner et al. .............. 2/161.7 |
| 5,368,867 | A | 11/1994 | Da Silva et al. |
| 5,419,908 | A | 5/1995 | Richter et al. |
| 5,437,858 | A | 8/1995 | Hungerbach et al. |
| 5,494,644 | A | 2/1996 | Thomas et al. |
| 5,508,046 | A | 4/1996 | Cosentino et al. |
| 5,563,132 | A | 10/1996 | Bodaness |
| 5,709,870 | A | 1/1998 | Yoshimura et al. |
| 5,824,267 | A | 10/1998 | Kawasumi et al. |
| 5,875,889 | A | 3/1999 | Albisetti |
| 5,945,032 | A | 8/1999 | Breitenbach et al. |
| 5,951,993 | A | 9/1999 | Scholz et al. |
| 5,977,403 | A | 11/1999 | Byers |
| 5,997,585 | A | 12/1999 | Scialla et al. |
| 6,021,892 | A | 2/2000 | Baudin |
| 6,027,469 | A | 2/2000 | Johnson |
| 6,114,298 | A | 9/2000 | Petri et al. |
| 6,197,814 | B1 | 3/2001 | Arata |
| 6,200,946 | B1 | 3/2001 | Blum et al. |
| 6,218,351 | B1 | 4/2001 | Busch et al. |
| 6,231,848 | B1 | 5/2001 | Breitenbach et al. |
| 6,242,009 | B1 | 6/2001 | Batarseh et al. |
| 6,257,253 | B1 | 7/2001 | Lentsch et al. |
| 6,277,414 | B1 | 8/2001 | Elhaik et al. |
| 6,293,433 | B1 | 9/2001 | Joulia |
| 6,302,968 | B1 | 10/2001 | Baum et al. |
| 6,306,812 | B1 | 10/2001 | Perkins et al. |
| 6,368,611 | B1 | 4/2002 | Whitbourne et al. |
| 6,379,712 | B1 | 4/2002 | Yan et al. |
| 6,436,342 | B1 | 8/2002 | Petri et al. |
| 6,540,791 | B1 | 4/2003 | Dias |
| 6,569,353 | B1 * | 5/2003 | Giletto et al. .......... 252/186.28 |
| 6,583,176 | B2 | 6/2003 | Arata |
| 6,630,172 | B2 | 10/2003 | Batarseh |
| 6,660,289 | B1 | 12/2003 | Wilmotte et al. |
| 6,743,348 | B2 | 6/2004 | Holladay et al. |
| 6,797,302 | B1 | 9/2004 | Ben Yehuda et al. |
| 6,827,766 | B2 | 12/2004 | Carnes et al. |
| 6,866,145 | B2 | 3/2005 | Richards et al. |
| 6,939,564 | B2 | 9/2005 | Ranger et al. |
| 6,939,566 | B2 | 9/2005 | Batarseh et al. |
| 6,959,807 | B2 | 11/2005 | Sharon et al. |
| 6,962,714 | B2 | 11/2005 | Hei et al. |
| 7,033,511 | B2 | 4/2006 | Zawada et al. |
| 7,083,043 | B2 | 8/2006 | Sharon |
| 2002/0137648 | A1 | 9/2002 | Sharma et al. |
| 2003/0008797 | A1 | 1/2003 | Hage et al. |
| 2003/0099717 | A1 | 5/2003 | Cabrera |
| 2003/0235623 | A1 | 12/2003 | Van Oosterom |
| 2004/0067159 | A1 | 4/2004 | Carnes et al. |
| 2004/0170742 | A1 | 9/2004 | Yehuda et al. |
| 2004/0234569 | A1 | 11/2004 | Nakada et al. |
| 2005/0013836 | A1 | 1/2005 | Raad |
| 2005/0194357 | A1 | 9/2005 | Liu et al. |
| 2005/0256017 | A1 | 11/2005 | Dykstra |
| 2005/0256200 | A1 | 11/2005 | Burkhart et al. |
| 2006/0035808 | A1 | 2/2006 | Ahmed et al. |
| 2006/0122082 | A1 | 6/2006 | Paul |
| 2006/0182813 | A1 | 8/2006 | Holladay |
| 2006/0198798 | A1 | 9/2006 | Tichy et al. |
| 2006/0198876 | A1 | 9/2006 | Tichy et al. |
| 2006/0199752 | A1 | 9/2006 | Tichy et al. |
| 2006/0240381 | A1 | 10/2006 | Rizoiu et al. |
| 2006/0263239 | A1 | 11/2006 | Tichy et al. |
| 2007/0048175 | A1 | 3/2007 | Tichy et al. |
| 2007/0053850 | A1 | 3/2007 | Tichy et al. |
| 2007/0059202 | A1 | 3/2007 | Tichy et al. |
| 2007/0059255 | A1 | 3/2007 | Tichy et al. |
| 2007/0254044 | A1 | 11/2007 | Karandikar et al. |

FOREIGN PATENT DOCUMENTS

| | | |
|---|---|---|
| WO | WO 03/080231 | 10/2003 |
| WO | WO 2005/000324 | 1/2005 |
| WO | WO 2006/079109 | 7/2006 |

OTHER PUBLICATIONS

Schuster, A. et al., "Persistent silver disinfectant for the environment: Myth and reality," Am. J. Infect. Control, Jun. 2003, pp. 309-311, vol. 32.

Brady, Michael J. et al., "Persistent silver disinfectant for the environmental control of pathogenic bacteria," Am. J. Infect. Control, Aug. 2004, pp. 208-214, vol. 31 (4).

Brentano, Loreno et al., "Antibacterial efficacy of a colloidal silver complex," Surg. Forum, 1966, pp. 76-78, vol. 17.

Phillips, Charles R., et al., "Chemical Disinfectant," Annual Review of Microbiology, Oct. 1958, pp. 525-550, vol. 12.

Monarca, S. et al, "Decontamination of dental unit waterlines using disinfectants and filters," Abstract Only, Minerva Stomatol., Oct. 2002, vol. 10.

Yin, Huiyong, "Analysis of Diacyl Peroxides by Ag+ Coordination Ionspray Tandem Mass Spectrometry: Free Radical Pathways of Complex Decomposition," J. Am. Soc. Mass Spectrum, Apr. 2001, pp. 449-455, vol. 12 (4).

Surdeau, N. et al, Sensitivity of bacterial viofilms and planktonic cells to a new antimicrobial agent, Oxsil 320N, Journal of Hospital Infection 2006, 62, 487-493, www.elsevierhealth.com/journals/jhin.

http://web.archive.org/web/20060217191603/http://sanosilbiotech.com/start_food.html, Virosil F&B, "Swift Virucidal with Swiss Precision," Feb. 17, 2006, 5 pages.

The interaction of silver ions and hydrogen peroxide in the inactivation of E coli: a preliminary evaluation of a new long lasting residual drinking water disinfectant; Water Science and Technology vol. 31 No. 5-6 pp. 123-129 (1995).

\* cited by examiner

FIG. 5

DEVICES, SYSTEMS, AND METHODS FOR DISPENSING DISINFECTANT SOLUTIONS COMPRISING A PEROXYGEN AND TRANSITION METAL

The present application is a continuation-in-part of U.S. patent application Ser. No. 11/514,721, filed on Aug. 31, 2006, which is a continuation-in-part of U.S. patent application Ser. Nos. 11/361,836, 11/361,841, 11/361,837, and 11/361,665, each of which was filed on Feb. 24, 2006, and each of which claims the benefit of U.S. Provisional Patent Application No. 60/656,723, filed on Feb. 25, 2005, and each of which are incorporated herein by reference in their entireties.

FIELD OF THE INVENTION

The present invention is drawn to disinfectant dispensing devices and systems which are used for disinfecting a variety of surfaces. The devices and systems are convenient, easy and safe to use.

BACKGROUND OF THE INVENTION

Disinfectants, such as hard surface disinfectants, are widely used in both domestic and professional settings. Exemplary of a commonly used hard surface cleaner is Lysol® disinfectant. Though Lysol® is effective for many applications; Lysol® is not as effective at reducing levels of bacterial endospores as commercially available glutaraldehyde aqueous solutions. Glutaraldehyde aqueous solutions are widely used as disinfectants, and are commonly available in 1 wt % and 2 wt % solutions, particularly in medical and dental settings. Glutaraldehyde solutions are typically used for more delicate medical/dental instruments that would otherwise be susceptible to damage by other sterilization methods, e.g., autoclaving. However, glutaraldehyde is also a powerful irritant and respiratory sensitizer. In fact, there have been reports of sensitization of individuals due to the fumes, which have lead to respiratory problems, headaches, lethargy, discoloring of the skin, etc. Because of these issues related to glutaraldehyde fumes, air quality must often be monitored, or appropriate air ventilation must be present. As a result, though glutaraldehyde solutions are relatively effective disinfectants, it would be desirable to provide compositions that can exhibit even more effective bacteria kill levels, and at the same time be safer for the individuals using the disinfectant.

SUMMARY OF THE INVENTION

It has been recognized that it would be desirable to provide systems and devices to effectively utilize disinfectant compositions that can show a high level of activity at the time of use. Many disinfectants on the market, while at the time of manufacture may be viable and useful as disinfectant compositions, at the time of use, such compositions have become unstable and/or have lost their potency or ability to disinfect with the passage of time. Therefore, it would be desirable to provide devices to effectively provide disinfectant compositions with high levels of activity at the time of desired use.

In accordance with this, a dispensing device can comprise a first compartment containing a first liquid composition and a second compartment containing a second liquid composition. The first liquid composition can include one or a plurality of transition metal(s) or alloy(s) thereof, and the second liquid composition can include one or a plurality of peroxygen(s). When brought together, the first and second liquid compositions for a disinfectant solution.

Likewise, a system for dispensing a disinfectant solution can comprise a first compartment containing a first liquid composition and a second compartment containing a second liquid composition. The first liquid composition can include a transition metal or alloy thereof and the second compartment can include a peroxygen. The system further includes a separator between the first and second compartments which can be modified or removed to cause the first liquid composition and the second liquid composition to contact one another.

Additionally, a method of disinfecting a surface can comprise providing a first compartment containing a first liquid composition comprising a transition metal or alloy thereof; and providing a second compartment, separated from the first compartment, containing a second liquid composition comprising a peroxygen. Other steps include bringing together the first liquid composition and the second liquid composition to form a disinfectant solution within a device which comprises the first compartment and the second compartment, and applying the disinfectant solution to the surface.

Additional features and advantages of the invention will be apparent from the detailed description that follows, which illustrates, by way of example, features of the invention.

BRIEF DESCRIPTION OF THE DRAWINGS

The drawings will be described further in connection with the following detailed description. Further, these drawings are not necessarily to scale and are by way of illustration only such that dimensions and geometries can vary from those illustrated. It should be further noted that the drawings show schematic side views of apparent square- and cubic-based devices in accordance with embodiments of the present invention. This shape is provided for ease of describing and providing an understanding of the invention. Thus, other shapes or configurations are possible, and often, even desirable.

DETAILED DESCRIPTION OF THE PREFERRED EMBODIMENT(S)

Reference will now be made to the exemplary embodiments, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention. It is also to be understood that the terminology used herein is used for the purpose of describing particular embodiments only. The terms are not intended to be limiting unless specified as such.

It must be noted that, as used in this specification and the appended claims, the singular forms "a," "an," and "the" include plural referents unless the content clearly dictates otherwise.

The term "food grade" when used with respect to a composition of the present invention refers to a composition that is substantially free from ingredients which would be considered harmful or toxic to a mammal upon consumption above levels that are generally recognized as safe.

Generally, though sanitizers, sterilants, and disinfectants are used for the same purpose, i.e. to kill bacteria and/or viruses, etc., a sterilant composition exhibits a greater kill level compared to a disinfectant, which in turn has a better kill level than a sanitizer. This being stated, most applications require only. sanitizer or disinfectant levels bacteria/virus reduction, though other applications benefit considerably from the use of sterilants. For convenience, in the present disclosure, the term "disinfectant" is used generally and includes sanitizers, disinfectants, and sterilants unless the context dictates otherwise.

The term "solution" is also used throughout the specification to describe the disinfectant compositions of the present invention. However, as these "solutions" can include colloidal transition metals, these compositions can also be described as dispersions or suspensions. As the continuous phase is typically a solution, and the transition metal can be present in ionic and/or colloidal form, for convenience, these compositions will typically be referred to as "solutions" herein. Further, sometimes a disinfectant solution is referred to as a "resultant" disinfectant solution. This is to provide clarity that the disinfectant solution is a product of the mixing of the two-part systems described herein. This being stated, the terms "disinfectant solution" and "resultant disinfectant solution" can be used interchangeably herein.

The term "substantially free" when used with regard to the disinfectant compositions of the present invention refers to the total absence of or near total absence of a specific compound or composition. For example, when a composition is said to be substantially free of aldehydes, there are either no aldehydes in the composition or only trace amounts of aldehydes in the composition. Likewise, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have a general overall result as if absolute and total completion were obtained.

The term "peroxygen" refers to any compound containing a dioxygen (O—O) bond. Dioxygen bonds, particularly bivalent O—O bonds, are readily cleavable, thereby allowing compounds containing them to act as powerful oxidizers. Non-limiting examples of classes of peroxygen compounds include peracids, peracid salts, and peroxides such as hydrogen peroxide.

When referring to the term "alloy," it is understood that individual colloidal or metallic particles can be in the form of composites of multiple metals, or alloys can also include co-dispersions of multiple metals as separate particles.

The term "alcosol" is a term of art which refers to a solution of an alcohol and a colloidal metal (e.g. colloidal silver). Some alcosols may include some amount of water in addition to the alcohol and colloidal metal. Similarly, the term "hydrosol" is a term of art which refers to a solution of water and colloidal metal (e.g. colloidal silver).

The term "two-part" when referring to the systems of the present invention is not limited to systems having only two parts. For example, the system can be a concentrate, and thus, is actually a three part system, e.g., a first part including transition metal and alcohol, a second part including a peroxygen and water, and a third part of a diluting solvent for diluting the first part, the second part, and/or the resultant disinfectant solution. Non-limiting examples of diluting solvents include water, alcohols, or combinations thereof. When the diluting solvent is an alcohol, it can, but need not be the same alcohol or mixture of alcohols which are present in the first "part" of the system. Thus, "two-part" is specifically defined herein to mean, at least two parts, unless the context dictates otherwise.

As used herein, the term "wipe" or "wipes" is used as is common in the field, and typically includes nonwoven fabric(s), towel(s), towellete(s), napkin(s), etc., that includes a disinfectant solution soaked therein or coated thereon.

As used herein, "dose," "single dosage," or the like, refers to a variable and calculated quantity that can be application specific. This concept is best understood through examples. In the case of cleaning a single person's hands, a dose can be an amount sufficient to spread around and effectively disinfect the person's hands. In the case of applying a layer of disinfectant solution to a home or industrial surface, such as a counter-top in a kitchen or restaurant, a dose can be the amount of solution required to effectively cover the surface of the counter-top. As such, a dose for one counter-top may not be the same as another counter-top due to variations in size and desired amounts of disinfectant solution. Therefore, the quantity is application specific, but is a calculable quantity. That said, a dose can also include a little more solution than is required to complete the identified single use.

In describing embodiments of the present invention, reference will be made to "first" or "second" compartments or liquid compositions as they relate to one another and the drawings, etc. It is noted that these are merely relative terms, and a compartment or composition described or shown as a "first" compartment or composition could just as easily be referred to a "second" compartment or composition, and such description is implicitly included herein.

Concentrations, dimensions, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a weight ratio range of about 1 wt % to about 20wt % should be interpreted to include not only the explicitly recited limits of about 1 wt % and about 20 wt %, but also to include individual weights such as 2 wt %, 11 wt %, 14 wt %, and sub-ranges such as 10 wt % to 20 wt %, 5 wt % to 15 wt %, etc.

In accordance with these definitions and embodiments of the present invention, a discussion of the various devices, systems, and methods is provided; after which, more specific detail related to the liquid compositions and disinfectant solutions that can be incorporated therein will also be provided. This being said, it should be noted that various embodiments will be discussed as they relate to devices, systems, methods, and compositions. Regardless of the context of the specific details as they are discussed for any one of these embodiments, it is understood they such discussion relates to other all other embodiments as well.

In accordance with this, a dispensing device can comprise a first compartment containing a first liquid composition and a second compartment containing a second liquid composition. The first liquid composition can include a transition metal or alloy thereof, and the second liquid composition can include a peroxygen. The compartments can be configured to keep the liquids separate until use, or shortly before use. The liquids form a disinfectant solution when brought together. In one aspect, the disinfectant solution has greater kill potency for pathogens than either the first liquid composition or the second liquid composition when used alone.

Likewise, a system for dispensing a disinfectant solution can comprise a first compartment containing a first liquid composition and a second compartment containing a second liquid composition. The first liquid composition can include a transition metal or alloy thereof and the second compartment can include a peroxygen. The system further includes a separator between the first and second compartments which can be modified or removed to cause the first liquid composition and the second liquid composition to contact one another.

Additionally, a method of disinfecting a surface can comprise providing a first compartment containing a first liquid composition comprising a transition metal or alloy thereof; and providing a second compartment, separated from the first compartment, containing a second liquid composition comprising a peroxygen. Other steps include bringing together the first liquid composition and the second liquid composition to form a disinfectant solution within a device which comprises the first compartment and the second compartment, and applying the disinfectant solution to the surface.

The device and system can further include wipes, nozzles, delivery hoses, mixing apparatuses, etc., depending on the application. The disinfectant solution can further include alcohol and/or water, among other additives, which can be admixed with the first liquid composition, the second liquid composition, or as part of a third liquid.

Figure 1:
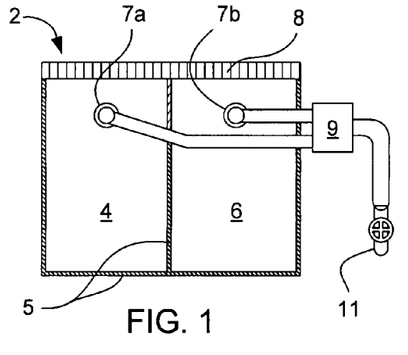
FIG. 1 is a schematic side view of a dispensing device, in accordance with one embodiment of the present invention.

Particularly useful for dispensing the solutions described above, a dispensing device of the present invention can include a first compartment and a second, separate, compartment. The first compartment can contain a first liquid composition which includes a transition metal or alloy thereof. The second compartment can contain a second liquid composition which contains a peroxygen. The first liquid composition and the second liquid composition can be formulated so that their combination forms a disinfectant solution. An aspect of this arrangement is illustrated in FIG. 1, wherein the dispensing device 2 includes a first compartment 4 and a second compartment 6. The first compartment and the second compartment are separated from each other by a housing 5. The illustrated embodiment further includes a lid 8. Also shown in this embodiment is a pair of nozzles 7a and 7b which are connected to a dispensing hose system 9. Although FIG. 1 shows the nozzles attached in an area of the housing near the lid, the location of each nozzle can be in any configuration which would allow for the passage of fluid from the respective compartment as the user desires. For example, the nozzle(s) could be nearer the side opposite the lid, in a corner or edge of the compartment area, and even on the bottom of the compartment. The dispensing hose system includes a pair of hoses that come together at a junction or mixing chamber, where the first liquid composition and the second liquid composition are mixed to form a disinfectant solution, and can be dispensed from a liquid sprayer 11. In one embodiment, the liquid sprayer can empty into a container. Dry wipes can be present in the container. Alternatively, wipes that are impregnated or pre-wetted with a liquid, e.g. water or the first liquid composition, can be present in the container.

Figure 2:
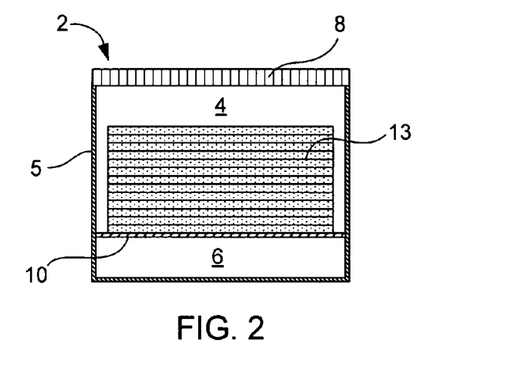
FIG. 2 is a schematic side view of a dispensing device, in accordance with another embodiment of the present invention.

In FIG. 2, the dispensing device 2 has a first compartment 4 and a second compartment 6 separated by a common wall 10. Again, the device includes a housing 5 and a lid 8. As illustrated, it would be a relatively simple process, depending on the material of the common wall, to break, modify, puncture, or remove the common wall and allow for the two liquids to contact one another and thus form a disinfectant solution. In the embodiment shown, the first compartment includes a stack of wipes 13 that are impregnated or soaked with the first liquid composition. When the common wall is modified or removed, the first liquid composition and the second liquid composition come together and form a disinfectant solution.

Such dispensing nozzle/hose/sprayer systems can be configured for variable spray, thus allowing for a variety of application types—including concentrated and dense liquid stream, fine spray, mist, aerosol, or even configured to produce a foam. In one embodiment, there may be two or more dispensing nozzles each connected to a separate compartment and configured so as to induce stream mixing at a rate sufficient to form a disinfectant solution prior to the time the liquids are applied to the surface.

In one aspect, the common wall 10, or another portion of one of the compartments may be frangible and easily broken or punctured. The modification, such as puncturing, can come from indirect or direct means. Direct means includes modifying the portion through such action as piercing the wall with a tool, or manually opening a flap by removing the flap, or by rotating a portion of the container to expose an opening, etc. Likewise, indirect means can include a design wherein a portion of one of the containers is modified or removed when safety packaging is tampered with. For example, such a device might include a frangible common wall that is configured to puncture or rip or otherwise breach when the device is opened for the first time (e.g. when force is applied to a safety strip that seals the lid closed). In one aspect, a device might include a separating wall wherein only a portion is frangible, e.g., a small area of the wall specifically configured for breaking while the remainder of the wall remains intact, or a connecting tube with a frangible seal. Furthermore, a portion of the common wall could be removable, or a portion thereof could be removable. Such could be effectuated by a sliding motion, where the common wall can be completely removed from the system, or even partially removed or opened so as to allow for liquid passage from one compartment into another. In such designs, desired mixing and application can be considered. For example, to effectuate passing substantially all of the liquid of one compartment into another compartment, the storage compartment can be placed at a height higher than the other compartment, and can rely on gravity to assist in fluid flow from one compartment to the other. Alternatively, the common wall can be breached or removed, and the device can be inverted to cause mixing. Another example may be a storage configuration where a common vertical wall separates the first and second compartments. In such case, removing the common wall can bring the liquids together. In some embodiments, the removable portion of a common wall may be replaceable. In further embodiments, the device can be configured so as to allow a set volume of fluid to pass through an open portion before the open portion is replaced or closed. Such a system could be automated to allow for a calculated dose of liquid at certain time intervals or in reaction to an external stimulus.

As shown in FIG. 2, the device can contain wipes 13. In such a device, the wipes can be included in the first compartment and/or the second compartment. In the embodiment shown, when the common wall is breached or removed, the liquid from the second compartment 6 mixes with the liquid from the first compartment, including the liquid impregnated or soaked into the wipes, causing the wipes to now contain the disinfectant solution for use. The wipes can be dry, or can be pre-wetted or saturated with liquids. In one aspect the wipes can be pre-wetted or immersed (partially or fully) in either the first liquid composition or the second liquid composition. Likewise, the wipes can be pre-wetted with an accelerating agent. Presently contemplated accelerating agents include a portion of the first liquid composition, a portion of the second liquid composition, and/or an alcohol, however any agent which can be incorporated into the wipes or placed thereon which induces an increase in the uptake of one or both of the first liquid composition and second liquid composition is to be included. If a smaller amount of liquid is impregnated in the wipes that the wipes are capable of absorbing, then the wipes can be said to be "hungry" for additional liquid, thereby facilitating liquid uptake by combining of the first liquid composition with the second liquid composition.

Figure 3:
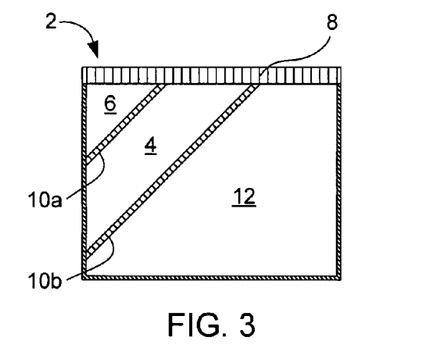
FIG. 3 is a schematic side view of a dispensing device, in accordance with another embodiment of the present invention, wherein the dispensing device includes a third compartment.

In one aspect, a third, or mixing, compartment could be included in the device. As with the first and second compartments, this compartment could be connected to the first and second compartments through pipes or tubes, and thus could be physically separated a distance from the first and/or second compartments. Alternatively, the third compartment could be included in the same compact device. In one aspect, the third compartment can substantially encompass one or both liquid-containing compartments. Such is the case in FIG. 3. In this embodiment, the third compartment 12 can be empty or not. In one aspect, the third compartment can contain one or more of the desired components of the disinfecting solution. For example, the third compartment could contain a peroxygen, identical to or different from (e.g. different peroxygen species, concentration, etc.) the peroxygen in the second compartment 6.

Again, in one aspect, the device can contain wipes (not shown in this embodiment). In such a device, the wipes can be included in the first compartment 4 and/or the second compartment 6. Furthermore, in some embodiments, the wipes can be included in a third compartment. For example, multiple wipes could be included in the third compartment 12 of FIG. 3. Further, as shown, the various compartments can be separated by common walls 10a, 10b, for example.

Figure 4:
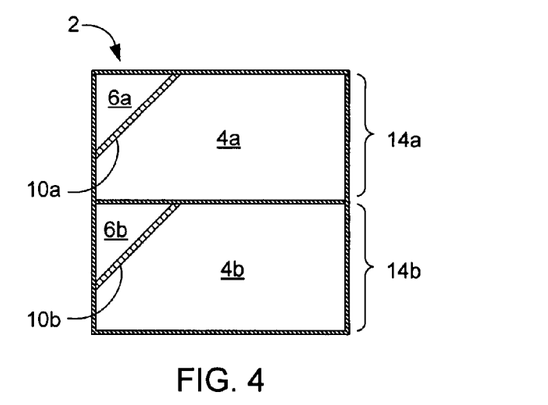
FIG. 4 is a schematic side view of a dispensing device, in accordance with another embodiment of the present invention, wherein the dispensing device includes multiple devices in a common housing.

A further design consideration which allows for both short and long term storage and use of a viably potent disinfectant solution includes device segments or individual device pods. Such separately defined pods within a device allow for bringing together an amount of the first liquid composition and the second liquid composition, while additional first and second liquid composition remains separated from each other and from the mixed disinfectant solution. This embodiment is illustrated in FIG. 4. The dispensing device 2 includes a first segment 14a, with a first compartment 4a and a second compartment 6aseparated by a common wall 10a. A second segment 14b includes a first compartment 4b and a second compartment 6b separated by a common wall 10b. Although only two segments are illustrated, multiple segments could be used in series, parallel, or other configuration. Thus, a dose of a disinfectant solution can be obtained from combining the first liquid composition and the second liquid composition from compartments 4a and 6a, without disturbing the separation of the first liquid composition and the second liquid composition from compartments 4b and 6b, which can be combined and used at a later time.

Figure 5:
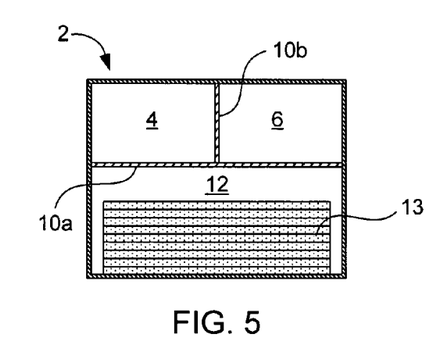
FIG. 5 is a schematic side view of a dispensing device, in accordance with another embodiment of the present invention, wherein the dispensing device includes a third compartment with wipes.

Another configuration is illustrated generally at 2 in FIG. 5, wherein the first compartment 4 and the second compartment 6 are separated by a common wall 10a. Both the first compartment and the second compartment are individually separated from a third compartment 12 by another common wall 10b. The third compartment includes wipes 13. As with other embodiments, the wipes can be dry and the third compartment can be substantially free of liquid. Alternatively, the wipes can be pre-moistened by any of a variety of liquids, such as the first liquid composition. In this particular embodiment, the first and second liquid compositions can first combine by the breaking or otherwise breaching of common wall 10a, followed by wetting the wipes caused by breaching common wall 10b. Alternatively, common wall 10b can be configured to break while common wall 10a remains substantially in tact, thus allowing the first and the second liquid compositions to enter and combine in the third compartment. In a further embodiment, both common walls 10a and 10b can be configured to allow passage of liquid at substantially the same time, thus permitting the first and second liquid compositions to combine in any and possibly all of the three compartments.

The amount of the first and the second liquid composition in the device can be adjusted, according to concentrations and the size of the container to produce a disinfectant solution when the first and the second liquid compositions are brought together. Therefore, any amount of each liquid, which produces a disinfectant solution, is contemplated by the present invention. In one aspect, the amount of the first and second liquid composition in the device can be adjusted and formulated to allow for a volume ratio of the first liquid composition to the second liquid composition from about 10:1 to about 1:10. Likewise, a volume ratio from about 5:1 to about 1:5, and even a volume ratio from about 2:1 to about 1:2, may be used in the present design. In some aspects, the liquid in the first compartment and the liquid in the second compartment can be single dose amounts. Such may be useful in the case of a single wipe or in single-dose packs for transportation or inclusion in first-aid kits or other assorted packaging.

The dispensing device and system presented herein provide an effective way to form a disinfectant solution that is viable and useful at the time of desired use. Many systems and devices presently on the market, particularly with wipes, prove that the majority of disinfecting solutions degrade over time and lose their viable potency. By using the present system and device, it is possible to present a viable disinfectant solution after short or long term storage. As such, it may be useful to design the first compartment and/or the second compartment for long term storage. Such design would include selection of materials to manufacture the compartment(s) which are substantially unreactive with the enclosed liquid, and unreactive and/or robust to the outside environment. In one aspect, such material may be a polymer or other material that is inert with respect to the components.

In some embodiments, it may be desirable or useful to prepare a concentrated disinfectant solution. In such case, the amount of peroxygen and the amount of transition metal or alloy thereof would be higher than that in the desired final disinfectant solution. In one aspect, the diluent may be water or another substance. In one embodiment, the diluent can be admixed with the first and second liquid compositions using a nozzle, similar to that shown in FIG. 1, from a third compartment or an external source.

Before the first and second liquid compositions are brought together, or after the first and second liquid compositions are brought together (either within the compartments or outside of the compartments), individual components or the mixed disinfectant solution may be modified to any form useful for application, such as in the form of a gas, fog, foam, gel, etc. In the case of gel formation, a gelling agent may be added to the disinfectant solution to produce such gel. Appropriate gelling agents that can be used include polyvinyl alcohol, polyvinyl pyrrolidone, etc.

In one aspect, the dispensing device may include a pump. Such pump can be configured to work with a dispensing nozzle, and can be designed for manual operation or automatic operation. Manual pumps that can be used include those commonly included in ordinary lotion and/or hand soap dispensers. In another aspect, the pump can be configured for automatic operation, and can be designed to run on a timer. In one embodiment, the pump can be placed so as to draw disinfectant solution from the device and eject the liquid from the device. In an alternate design, the pump can be configured to draw liquid from one compartment (e.g. the first compartment or the second compartment) and eject the liquid into the other compartment or a third compartment. Such design can be used to effectuate mixing. A pump can be designed to dispense a single dose.

The device and system can be configured for a variety of environments. In one aspect, the first and second compartments and optional third compartment, etc. may be surrounded by an outer shell. The outer shell can be designed to handle specific environmental conditions, and/or can be designed to allow for selective replacement of one or both liquids and/or compartments. In one aspect, the device, or portions thereof, may be substantially flexible. Further, in other aspects, the device may include one or more handles and/or wheels to aid in handling and transport of the dispensing device.

With more specific detail related to the various liquid compositions that can be used, a two-part disinfectant system can comprise a first liquid composition and a second liquid composition. The first liquid composition can comprise from 0.0005 ppm to 100,000 ppm by weight of a transition metal or alloy and an alcohol, and the second liquid composition can comprise water and a peroxygen compound. The first and second liquid compositions can be formulated to be combined so as to yield a resultant disinfectant solution.

In another embodiment, a method of disinfecting a surface can comprise admixing a first liquid composition and a second liquid composition to form a resultant disinfectant composition. The first liquid composition can comprise from 0.0005 ppm to 100,000 ppm by weight of a transition metal or alloy and an alcohol, the second liquid composition can comprise water and a peroxygen compound. The method further comprises contacting the resultant disinfectant with a surface, thereby disinfecting the surface. The contacting can occur after the resultant disinfectant is formed, or can form after both parts are contacted with the surface.

In these embodiments, it is notable that the concentrations of each ingredient can be described in the context of concentration in the first or second liquid composition, or the resultant disinfectant solution. The concentration of a compound in the first or second liquid composition will usually be lower in the resultant disinfectant solution than in the first or second liquid composition, as the amount typically gets diluted by the other part of the system. This being stated, this is not always the case, depending on the ingredients in the other portion of the two-part system.

In embodiments of the present invention, the alcohol can be present in the first liquid composition at from about 0.005 wt % to 99.99 wt %, with the upper end of the range being modifiable to 80 wt % or 50 wt %, and the lower end of the range being modifiable to 0.05 wt % or 0.1 wt %. This being stated, it is also noted that in certain embodiments, the alcohol can be present in the resultant disinfectant solution at from 0.001 wt % to 95 wt %, with the lower end of the range being modifiable to 0.05 wt % or 0.1 wt %, and the upper end of the range being modifiable to 40 wt %, 30 wt %, 20 wt % or 10 wt % in accordance with embodiments of the present invention. Any combination of these upper and lower limits is included herein.

Regarding the transition metal or alloy present in the first liquid composition, the range of 0.0005 ppm to 100,000 ppm by weight can be modified at the upper end of the range to 20,000 ppm or 5,000 ppm, and/or can be modified at the lower end of the range to 0.001 ppm, 0.01 ppm, or 1 ppm. The resultant disinfectant solution, on the other hand, can include from 0.001 ppm to 50,000 ppm by weight of the transition metal or alloy thereof. This range can be modified at the upper end of the range to 10,000 ppm, 5,000 ppm, or 1,500 ppm, and at the lower end of the range from 0.1 ppm, 1 ppm, or 15 ppm, for example. Any combination of these upper and lower limits is included herein.

Regarding the second liquid composition, water and the peroxygen compound can be present at various ratios. For example, the peroxygen can be present in the second liquid composition at from 0.001 wt % to 80 wt %, with the upper end of the range being modifiable to 30 wt % or 15 wt %, and the lower end of the range being modifiable to 0.01 wt % or 0.05 wt %. Regarding the resultant disinfectant solution, the peroxygen content can be, for example, from 0.01 wt % to 20 wt %, with the upper end of the range being modifiable to 10 wt %, 5 wt %, or 2 wt %, and the lower end of the range being modifiable to 0.01 wt %, 0.2 wt %, or 0.3 wt %. Again, any combination of these upper and lower limits is included herein. Additionally, many peroxygens have a concentration in which they are considered stable for long-term storage conditions. Such considerations can be taken into account when formulating the second liquid composition. In one example, some peroxygens tend to be stable for longer periods of time in a range above about 14 wt %. In that case, an aspect of the invention may include the peroxygen content at greater than about 14 wt %, which can be diluted to a much lower concentration just prior to use by admixing with the first or other liquid.

As these ranges are merely exemplary, one skilled in the art could modify these ranges for a particular application, considering such things as the type of alcohol (polyhydric, food grade, mixtures, etc.); the type of peroxygen (peroxide, peracid, combination of peroxide/peracid, etc.); and the type of metal (ionic, colloidal, alloy, etc.).

The systems and methods can be formulated and packaged in any manner known to those skilled in the art so long as it allows the two liquid compositions of the system to remain separate until shortly before the desired use of the disinfectant solution. In one embodiment, the two liquid compositions of the system can be contained in separate containers such as bottles, jars, bags, dispensers, etc. In one aspect of the invention, the system can be configured and the liquid compositions formulated so that the disinfectant solution can be made from the two liquid compositions alone. In another aspect of the invention, the two liquid compositions of the system can be formulated to provide a concentrate of the disinfectant solution which can be diluted to a desired disinfectant potency level with water or other diluting solvent(s).

In another embodiment of the present invention, the two liquid compositions of the system can be placed in separate compartments of a single container. For example, the system can comprise a two compartment container, each compartment having a separate extraction tube for extracting the liquid compositions in the compartments. In one aspect, the container can include a spray nozzle connected to the two extraction tubes. The two liquid compositions can be drawn up the extraction tubes to a mixing chamber within the spray nozzle and then discharged from the nozzle and onto the surface being disinfected. In this embodiment, the disinfectant solution is effectively made in small batches within the mixing chamber and discharged for use shortly after combination of the two liquid compositions.

The system can be convenient, easy to use and package, and can have a prolonged shelf life. Typically, disinfectant compositions containing peroxygen compounds degrade fairly quickly when combined with other agents, therefore rendering their shelf life undesirably short. The present invention provides a system which maintains the peroxygen compound separate from the rest of the disinfectant solution until shortly before its use. Such a configuration of the system allows for the disinfectant solution to effectively have a prolonged shelf life. This is particularly helpful where the liquids of the system are intended to be sold in retail and wholesale businesses, as storage, transportation, and end point shelf times can be substantial.

In one embodiment, the disinfectant solution, and hence the two liquid compositions of the two-part system, can include only ingredients that are food-grade or food safe. For example, though not required, the composition can be substantially free of disinfectant ingredients commonly present in many commercially available surface cleaners. Examples of non-food-grade ingredients which can be omitted from the disinfectant solution include, but are not limited to, aldehydes such as glutaraldehyde; chlorine-based disinfectants; chlorine and bromine-based disinfectants; iodophore-based disinfectants; phenolic-based disinfectants, quaternary ammonium-based disinfectants; and the like.

The liquid compositions of the present invention can also include other ingredients, such as organic co-solvents, surfactants, excipients, fillers, colorant, other active ingredients, ingredients that may be present in the other part, etc. In one embodiment, the first liquid composition can include water in addition to the alcohol.

Examples of alcohols which can be used in the first liquid composition include but are limited to aliphatic alcohols and other carbon-containing alcohols, having from 1 to 24 carbons ($C_1$-$C_{24}$ alcohol). It is to be noted that "$C_1$-$C_{24}$ alcohol" does not necessarily imply only straight chain saturated aliphatic alcohols, as other carbon-containing alcohols can also be used within this definition, including branched aliphatic alcohols, alicyclic alcohols, aromatic alcohols, unsaturated alcohols, as well as substituted aliphatic, alicyclic, aromatic, and unsaturated alcohols, etc. In one embodiment, the aliphatic alcohols can be $C_1$ to $C_5$ alcohols including methanol, ethanol, propanol and isopropanol, butanols, and pentanols, due to their availability and lower boiling points. This being stated, polyhydric alcohols can also be used effectively in enhancing the disinfectant and sterilant potency of the disinfectant solution of the present invention, as well as provide some degree of added stabilization. Examples of polyhydric alcohols which can be used in the present invention include but are not limited to ethylene glycol(ethane-1,2-diol)glycerin (or glycerol, propane-1,2,3-triol), and propane-1,2-diol. Other non-aliphatic alcohols may also be used including but not limited to phenols and substituted phenols, erucyl alcohol, ricinolyl alcohol, arachidyl alcohol, capryl alcohol, capric alcohol, behenyl alcohol, lauryl alcohol (1-dodecanol), myristyl alcohol (1-tetradecanol), cetyl (or palmityl) alcohol (1-hexadecanol), stearyl alcohol (1-octadecanol), isostearyl alcohol, oleyl alcohol (cis-9-octadecen-1-ol), palmitoleyl alcohol, linoleyl alcohol (9Z,12Z-octadecadien-1-ol), elaidyl alcohol (9E-octadecen-1-ol), elaidolinoleyl alcohol (9E, 12E-octadecadien-1-ol), linolenyl alcohol (9Z, 12Z, 15Z-octadecatrien-1-ol), elaidolinolenyl alcohol (9E, 12E,15-E-octadecatrien-1-ol), combinations thereof, and the like.

In some embodiments, for practical considerations, methanol, ethanol, and denatured alcohols (mixtures of ethanol and smaller amounts of methanol, and optionally, minute amounts of benzene, ketones, acetates, etc.) can often be preferred for use because of their availability and cost. Glycerol can also be preferred in some embodiments. If the desire is to provide a food grade composition, then alcohols can be selected that satisfy this requirement. When considering the amount of alcohol to use, one skilled in the art can stay within the above-described ranges, or modify these ranges for a particular application, considering such things as whether alcohol selected for use is polyhydric, whether the alcohol is food grade, mixtures of alcohols, etc.

Regarding the transition metal present in the first liquid composition, and ultimately in the disinfectant solution, the metal can be in ionic form (e.g. disassociate metal salt, metal ions from elemental metal, etc.) and/or in colloidal form. In one specific embodiment, the transition metal can be in a sub-micron form (i.e. dispersion of less than 1 µm metal colloidal particles). However, larger colloidal transition metal particles can also be used in certain applications. Typical transition metals that are desirable for use include Group VI to Group XI transition metals, and more preferably, can include Group X to Group XI transition metals. Alloys including at least one metal from the Group VI to Group XI metals can also be used. As shown below in the examples, some alloys can enhance or increase the disinfectant potency of the present invention. It is recognized that any of these metals will typically be oxidized to the corresponding action in the presence of a peroxygen. However, with colloidal metals, typically, the surface is usually more susceptible to such oxidation. Further, when colloidal metals are dispersed in a colloidal solution, there is often an amount of the metal in ionic or salt form that is also present in the suspension solution. For example, colloidal silver may include a certain percentage of silver salt or ionic silver in solution, e.g., 10% to 90% by weight of metal content can be ionic based on the total metal content. This being stated, certain preferred metals for use in accordance with embodiments of the present invention are ruthenium, rhodium, osmium, iridium, palladium, platinum, copper, gold, silver, manganese, zinc, alloys thereof, and mixtures thereof. Silver is often the most preferred, but metal choice can be dependent to some degree on the application, the levels of kill desired or required, the type of pathogen being targeted, the substrate that is being cleaned, etc.

It is also noted that any of these embodiments can often also benefit from the use of alloys. For Example, certain combinations of metals in an alloy may provide an acceptable kill level for a specific pathogen, and also provide benefits that are related more to secondary consideration, such as solution stability, substrate to be cleaned, etc. Preferred examples of transition metal alloys for use in the present invention include but are not limited to copper-silver alloys, silver-manganese alloys, iron-copper alloys, chromium-silver alloys, gold-silver alloys, magnesium-silver alloys, and the like.

Exemplary colloidal silvers that can be used in the first liquid composition include those sold by Solutions IE, Inc. under the trade names CS Plus and CS Ultra. Other colloidal silver products that can be used as the silver source include ASAP, Sovereign Silver, Silver Max, and the like. In one embodiment, the colloidal particles used in the present invention can have a particle size range of nano to micron size. In one embodiment, the particles can have a size range of 1.0 nm to 1.0 μm. In a more detailed embodiment, the particle size range can be from 0.001 μm to 1.0 μm. In another embodiment the colloidal transition metal particles can have a size range of from 0.030 μm to 0.5 μm. In still another embodiment the average particle size is 0.35 μm to 0.45 μm. If used in ionic form, preferred silver salts include but are not limited to silver nitrate, silver acetate, silver citrate, silver oxide, and/or silver carbonate. Though many colloidal silver solutions or ionic silver solutions that are functional for use in the formulations of the present invention can be used, in one embodiment, it can be desirable to use RO water as the suspension medium for the colloidal and/or ionic silver that is mixed with the other ingredients. In a more detailed aspect, the RO water can also be distilled, resulting in 18-20 MΩ water, though this is not required.

The peroxygen component of the second liquid composition, and ultimately the disinfectant solution, can be a single compound or a combination of multiple peroxygen compounds or peroxygen forming compounds. In one embodiment, the peroxygen can be any aliphatic or aromatic peracid (or peroxyacid) that is functional for disinfectant purposes in accordance with embodiments of the present invention. While any functional peroxyacid can be used, peroxyacids containing from 1 to 7 carbons are the most practical for use. These peroxyacids can include, but not be limited to, peroxyformic acid, peroxyacetic acid, peroxyoxalic acid, peroxypropanoic acid, perlactic acid, peroxybutanoic acid, peroxypentanoic acid, peroxyhexanoic acid, peroxyadipic acid, peroxycitric, and/or peroxybenzoic acid. The peroxyacid used in the present invention can be prepared using any method known in the art. When the peroxyacid is prepared from an acid and hydrogen peroxide, the resultant mixture contains both the peroxyacid and the corresponding acid that it is prepared from. For example, in embodiments that utilize peroxyacetic acid, the presence of the related acid (acetic acid) provides stability to the mixture, as the reaction is an equilibrium between the acid, hydrogen peroxide, and the peroxyacid and water, as follows:

$$H_2O_2 + CH_3COOH \leftrightarrows CH_3COO-OH + H_2O$$

Peracid salts, such as salts of the above listed peracids, can also be included as the peroxygen component of the disinfectant solutions. Non-limiting examples of such salts include permanganates, perborates, perchlorates, peracetates, percarbonates, persulphates, and the like. The salts can be used alone or in combination with each other or other peroxygen compounds to form the peroxygen component of the invention.

In another embodiment, the peroxygen component of the invention can include a peroxide compound. While hydrogen peroxide is considered to be a desirable peroxide for use in accordance with embodiments of the present invention, other peroxides can also be used, such as metal peroxides and peroxyhydrates. The metal peroxides that can be used include, but are not limited to, sodium peroxide, magnesium peroxide, calcium peroxide, barium peroxide, and/or strontium peroxide. Other salts (for example sodium percarbonate) have hydrogen peroxide associated therewith much like waters of hydration, and these could also be considered to be a source of hydrogen peroxide, thereby producing hydrogen peroxide in situ. As mentioned above, the peroxides can be used alone or in combination with other peroxygen compounds to form the peroxygen component of the present invention. In one embodiment the peroxygen is a peracid and a peroxide.

Once the disinfectant solution of the present invention is formed using the system, it can be used to disinfect any number of objects using any number of contacting methods. For example, the disinfectant solution can be used as a liquid dispersion bath for objects such as instruments or as a spray for applying to less mobile objects. The disinfectant solution can also be used as a topical dressing or a mouthwash. In other words, any application method known by those skilled in the art can be utilized in accordance with embodiments of the present invention. Other possible applications or methods of use for the disinfectant solution include, without limitation, use as a wipe where the liquid dispersion is applied to a fabric or fabric-like material for easy application without the need for spray or other application methods, use as a topical dressing, use as a mouthwash, etc. In other words, any application method known by those skilled in the art can be utilized in accordance with embodiments of the present invention.

Additionally, though the disinfectant solution of the present invention is described generally as a disinfectant, it is recognized that there are many possible applications including its use as a sterilant or sanitizer. For example, without limitation, the disinfectant solution of the present invention can be used to kill bacteria, spores, viruses, parasites, funguses, and molds. As described, this composition can be used against all of these types of organisms with relative to complete safety to humans and other mammals.

Another feature of the disinfectant solutions of the present invention is that they have residual kill properties. Residual kill properties refer to the ability of the disinfectant solution to prevent the growth of or kill newly introduced organisms. For example, when a disinfectant solution made by the system of the present invention is applied to a surface, they act to kill existing bacteria, viruses, and/or funguses. The residual kill characteristic of the disinfectant solutions allow the solutions to continue to kill any newly introduced pathogens which may contact the surface, even after the evaporation of the solvents in the disinfectant solutions. The disinfectant solutions of the present invention are capable of providing residual kill characteristics to a contacted surface for long periods of time so long as the disinfectant solutions are not mechanically removed (e.g. washing, scraping, etc). In some embodiments, the residual kill can last for 15 days or more. In some instances when colloidal metal is present, the colloidal metal can remain on the surface indefinitely, providing antibacterial and/or antiviral benefits for long periods of time. Alternatively, if it is desired to maintain residual kill characteristics on a surface for a period of time longer than 15 days, additional applications of the disinfectant solution can be made. In this way, the disinfectant solution can also be used a prophylactic against pathogens. It is noteworthy that the residual kill property of the disinfectant solution is present regardless of the mode of preparation of the solution. In other words, a disinfectant solution prepared using the two-part disinfectant system of the present invention and one prepared using direct admixing of each of the same individual ingredients both have the residual kill property. Without being bound by any particular theory, it is believed that the metal content contributes to this residual kill, as the metal content can remain on the surface in elemental form, without degrading or evaporating.

Because the disinfectant solution can be formulated to be very safe, e.g., often including only food grade components, these compositions can be used in areas which extend well beyond their use as surface disinfectants. Such product categories include both topically and internally applied products for both humans and animals. For example, the disinfectant solution can be used for antiseptics, burn treatments, diaper rash products, and various skin care products. Alternatively, the disinfectant solutions can be used inside the mouth, such as for mouthwashes, toothpastes, and various other disinfecting solutions that are be employed in dental mold materials. As dental molds are known to spread significant disease in the dental industry, such use with dental molds can prevent or reduce the spread of pathogens from a patient's mouth to lab employees working with the finished molds. Still a further category of use includes application for antibiotic and antiviral purposes. The disinfectant solution can be formulated into lozenges or gums for application to the mouth and throat, and can even be administered orally, intramuscularly, intravenously, etc. Because of the kill levels that can be achieved, even when formulated with only food grade components, a wide range of pathogens, as well as some viruses, can be killed internally. Without being bound by any particular possibility, these compositions can be useful in killing various viruses such as HIV, SARS, West Nile, Bird Flu, and others.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example 1

Preparation of a Disinfectant Solution Using a Two-Part System

A two-part disinfectant system is provided. The first liquid composition of the system includes a solution of 20 parts by weight glycerol, 29.97 parts water and 0.03 parts colloidal silver (600 ppm). The second liquid composition includes, by weight, 1.3 parts peracetic acid and 48.7 parts water. The two components are kept separate until immediately before the disinfectant is desired for use. The disinfectant solution is made by mixing the two components at about a 1:1 (first:second) weight ratio to yield a composition having about 1.3 wt % peracetic acid and about 300 ppm silver. In this embodiment, less than 3 wt % of hydrogen peroxide can be added to further stabilize the system. This disinfectant solution can be used effectively to disinfect and sterilize a variety of surfaces.

Example 2

Preparation of a Disinfectant Solution Using a Two-Part System

A two-part disinfectant system is provided. The first liquid composition of the system includes a solution of about 10 parts by weight glycerol and about 81parts by weight of a silver hydrosol (300 ppm colloidal silver). The second liquid composition of the system includes an aqueous solution of 15 wt % peracetic acid in water. The two components are kept separate until immediately before the disinfectant is desired for use. The two components are combined at a weight ratio of 91:9 (first:second), yielding a solution having about 1.3 wt % peracetic acid. This disinfectant solution can be used effectively to disinfect and sterilize a variety of surfaces. It is noted that there will be less than 300 ppm by weight of the colloidal silver when based on the resultant disinfectant composition as a whole. This disinfectant solution can be used effectively to disinfect and sterilize a variety of surfaces.

Example 3

Preparation of a Disinfectant Solution Using a Two-Part System

A two-part disinfectant system is provided. The liquid composition of the system includes a solution of about 10 parts by weight glycerol and about 87parts by weight of a silver hydrosol (800 ppm colloidal silver). The second liquid composition of the system is an aqueous solution of 15 wt % peracetic acid. The two components are kept separate until immediately before the disinfectant is desired for use. The disinfectant solution is made by mixing the two components at about a 97:3 (first:second) weight ratio to yield a composition having about 0.4wt % peracetic acid. It is noted that there will be less than 300 ppm by weight of the colloidal silver when based on the resultant disinfectant composition as a whole. This disinfectant solution can be used effectively to disinfect and sterilize a variety of surfaces.

Example 4

Preparation of a Concentrated Disinfectant Solution Using a Two-Part System

A two-part disinfectant system is provided. The first liquid composition of the system is a solution of a silver alcosol (alcohol/3800 ppm silver). The second liquid composition of the system is an aqueous solution of 15 wt % peracetic acid. The two components are kept separate until immediately before the disinfectant is desired for use, and are admixed at a 17:13 (first:second) weight ratio. This resultant disinfectant solution can be further diluted using water. For example, 0.6 liters of the resultant disinfectant solution can be mixed with 2.4 liters of water to yield 3 liters of the disinfectant solution having 1.3 wt % PAA. This disinfectant solution can be used effectively to disinfect and sterilize a variety of surfaces.

Example 5

Preparation of a Disinfectant Solution Using a Two-Part System

A two-part disinfectant system is provided. The first liquid composition includes, by weight, 9 parts ethanol, 40.9 parts water, and 0.1 part silver (2,000ppm). The second liquid composition includes, by weight, 1.3 parts peroxypropanoic acid and 48.7 parts water. The two components are kept separate until immediately before the disinfectant is desired for use. The disinfectant solution is made by mixing the two components at about a 1:1(first:second) weight ratio to yield a composition having about 1.3 wt % peroxypropanoic acid and about 1,000 ppm silver. In this embodiment, less than 3 wt % of hydrogen peroxide can be added to further stabilize the system. This disinfectant solution can be used effectively to disinfect and sterilize a variety of surfaces.

Example 6

Preparation of a Disinfectant Solution Using a Two-Part System

A two-part disinfectant system is provided. The first liquid composition includes, by weight, 20 parts denatured alcohol, 29.45 parts water, and 0.05 parts silver and copper alloy (1,000 ppm). The second liquid composition includes, by weight, 3 parts percitric acid and 47 parts water. The two components are kept separate until immediately before the disinfectant is desired for use. The disinfectant solution is made by mixing the two components at about a 1:1(first: second) weight ratio to yield a composition having about 3 wt % percitric acid and about 500 ppm silver. In this embodiment, less than 3 wt % of hydrogen peroxide can be added to further stabilize the system. This disinfectant solution can be used effectively to disinfect and sterilize a variety of surfaces.

Example 7

Kill-Time Studies of *Mycobacterium bovis* Using a Resultant Disinfectant Solution A study was conducted to determine tuberculocidal activity when using resultant disinfectant solution which can be prepared in accordance with Example 1. The test was conducted on a hard surface using the CRA Environmental Wipe Method. This method is fully described in: Christensen, R. P., R. A. Robison, D. F. Robinson, B. J. Ploeger, R. W. Leavitt, and H. L. bodily, Antimicrobial Activity of Environmental Surface Disinfectants in the Absence and Presence of Bioburden. Journal of the American Dental Association, 119:493-505. 1989.

Specifically, a test suspension containing *Mycobacterium bovis* (ATCC # 35743) was prepared from a frozen suspension of a standardized culture grown in modified Proskauer-Beck medium. The suspension was thawed and mixed with an equal volume of phosphate-buffered gelatin solution in a Teflon-on-glass tissue grinder on ice. The suspension was homogenized for two minutes, then diluted 1:4 in physiological saline solution (PSS) containing 0.1% Tween 80. The suspension was vortexed and held on ice until used in inoculate the test surface.

A neutralizer mixture consisted of 50 ml flasks of Tryptic soy broth containing 1.0% Tween 80, 1.0% lecithin, and 50 µl of concentrated catalase solution (Sigma, C100, 42,300 units/mg).

The CRA environmental Wipe Method which was used is detailed below. An 8×12 inch piece of laminated plastic counter covering was secured to polypropylene dental trays (size B, Zirc Dental) with silicone adhesive. Lids and trays were sterilized by a hydrogen peroxide gas plasma sterilizer. Two ml of test organism suspension was applied to the surface with a sterile 2×2-in cotton-filled gauze sponge. The surface was allowed to dry 20-30 minutes in a biosafety cabinet under laminar flow. Then 3.5 ml of disinfectant (or water) was applied to a sterile gauze sponge, which was used to wipe the inoculated test surface for 10seconds using about 150-g pressure with overlapping strokes (20 left to right, followed by 20 top to bottom). After 3 minutes, the trays were flooded with 50ml of neutralizer and scrubbed for 1 minute with a sterile polypropylene brush to remove and suspend organisms. The fluid was collected and serially diluted 1:10in physiological saline solution (PSS). The number of viable organisms in selected dilution tubes was assayed by membrane filtration. One ml aliquots were plated in duplicate. The membranes were washed with about 100 ml of sterile PSS and removed to Mycobacteria 7H11 agar plates. The plates were incubated at 37° C. for about three weeks. The number of colonies on each was counted and log reduction and percent kill values were computed.

As a control, a titer of the test suspension was computed by performing membrane filtration assays of selected 1:10 dilutions of the test suspension in PSS. A neutralizer control was performed by inoculating a mixture of 9 ml of neutralizer and 1 ml of disinfectant with 100 µl of the $1:10^3$ dilution of the titer containing 1750 CFU. This produced 175 CFU/ml in the tube, which was allowed to stand for 20 minutes prior to dilution and assay of the tubes by membrane filtration using duplicate 1 ml samples.

The results are provided as follows:

TABLE 1a

*Mycobacterium bovis* Titer

| | Dilution | | |
|---|---|---|---|
| | $1:1 \times 10^3$ | $1:1 \times 10^4$ | $1:1 \times 10^5$ |
| Number of Colonies | TNC* TNC | TNC TNC | 175 174 |

*TNC—Too Numerous to Count

TABLE 1b

Disinfectant solution of Example 1
Dilution of *M. bovis*/disinfectant suspension

| | | Dilution | | |
|---|---|---|---|---|
| | Undiluted | $1:1 \times 10^1$ | $1:1 \times 10^2$ | $1:1 \times 10^3$ |
| 3 minutes | 1 | 0 0 | 0 0 | 0 0 |

TABLE 1c

Neutralization control
Undiluted 75
66

TABLE 1d

Sterility controls

| Material | Counts |
|---|---|
| Phosphate buffered gelatin | 0 |
| Neutralizer + catalas | 0 |
| Example 1 Disinfectant | 0 |
| Mycobacteria 7H11 Agar | 0 |
| Physiological sterile saline (PSS) + 0.1% Tween 80 | 0 |
| Physiological sterile saline (PSS) | 0 |

Results of the titer showed the initial concentration of *M. bovis* was 1.75×107 CFU per ml in the prepared suspension. Inoculation of the test surface following drying produced a challenge exhibited by the water control. The initial concentration of viable bacilli on the test surface (So) was $2.63\times10^5$. Results from these procedures allowed log reduction (LR) and percent kill (PK) values to be calculated using the formulas: 1) $LR=-Log(S/So)$ where S=concentration of viable organisms after a period of exposure to the disinfectant; and So=the initial concentration of viable organisms at time zero; These values are shown in the Table 20 below.

TABLE 2

| Solution | Contact Time | Results Log Reduction (LR) | Percent Kill (PK) |
|---|---|---|---|
| Example 1 | 3 minutes | 5.02 | 99.99905 |

The neutralization control data indicated that each test solution was adequately neutralized. Observed counts were similar to those expected from the titer data.

Example 8

Kill-Time Studies of Sporicidal Activity a Resultant Disinfectant Solution

A study was conducted to determine the antimicrobial activity of a silver-containing resultant disinfectant solution which can be prepared in accordance with Example 1. The study was conducted on bacterial endospores from the test organism *Bacillus subtilis*. This was accomplished by performing a standard kill-time suspension test using a suspension of *B. subtilis* endospores. In general, spores are much more difficult to kill than common bacteria.

The test suspension containing endospores from *Bacillus subtilis* (ATCC #19659) was prepared from a culture grown for three days at 37° C. in Leighton-Doi medium. The suspension was placed at 65° C. for 30 minutes to kill vegetative organisms, then centrifuged to pellet the spores. Spores were resuspended in sterile HPLC water and allowed to set overnight at 4° C. This washing/setting process was repeated a total of three times. The final spore suspension was examined for purity using phase-contrast microscopy and stored at 4° C. until used.

A neutralizer solution was also prepared that consisted of 9 ml tubes of 12.7 wt % Tween 80, 6.0 wt % Tamol, 1.7 wt % lecithin, 1 wt % peptone, and 1.0wt % cystine, and 500 mM tris (pH 7.85), to which 100 µl of catalase solution (Sigma, C100, 42,300 units/mg) was added immediately before use.

The "kill time" procedure was as follows: A 9.9 ml aliquot of the disinfectant was placed in a 50 ml polypropylene sterile centrifuge tube. The tube was equilibrated in a 20° C. water bath. The tube of disinfectant was inoculated with 100 µl of the spore suspension at time zero. After a 30 second contact time, one ml of spore/disinfectant suspension was removed to 9.1 ml of neutralizer. The tubes were mixed thoroughly. After 2 minutes, the neutralized suspension was serially diluted 1:10, in physiological saline solution in physiological saline solution (PSS). The number of viable spores in selected dilution tubes was assayed by membrane filtration. One (1) ml aliquots were plated in duplicate. The membranes were washed with about 100 ml of sterile PSS and removed to Columbia agar plates. The plates were incubated at 37° C. for 20 hours. The number of colonies on each filter was counted and log reduction and percent kill values were computed.

As a control, a titer of the test suspension was computed by performing membrane filtration assays on selected 1:10 dilutions in PSS of the test suspension. A neutralizer control was performed by inoculating a mixture of 9.1ml of neutralizer and 1 ml of disinfectant with 100 µl of the $1:1\times10^6$ dilution of the titer. This produced about 130 CFU/ml in the tube, which was allowed to stand for 20 minutes prior to dilution and assay by membrane filtration using duplicate 1ml samples.

The results are provided as follows:

TABLE 3a

*Bacillus Subtilis* Titer

| | Dilution | | |
|---|---|---|---|
| | $1:1 \times 10^7$ | $1:1 \times 10^8$ | $1:1 \times 10^9$ |
| Number of Colonies | TNC* TNC | 106 115 | 10 15 |

*TNC—Too Numerous to Count

TABLE 3b

Disinfectant solution (Example 1) Dilution of *B. subtilis* spores/disinfectant suspension

| | Dilution | | |
|---|---|---|---|
| | $1:1 \times 10^2$ | $1:1 \times 10^3$ | $1:1 \times 10^4$ |
| 30 Seconds | 0 0 | 0 0 | 0 0 |

TABLE 3c

Neutralization control Undiluted 135
118

TABLE 3d

Sterility Controls

| Material | Counts |
|---|---|
| PSS | 0 |
| Neutralizer | 0 |
| Columbia Agar | 0 |
| Example 1 | 0 |

Results of the titer showed a viable *B. subtilis* spore concentration of $1.11\times10^{10}$ spores per ml in the original suspension. Inoculation of 9.9 ml of disinfectant with 100 µl of this suspension produced an initial concentration of $1.11\times10^8$ spores per ml in the assay tube. Results from these procedures allowed log reduction (LR) and percent kill (PK) values to be calculated using the formulas: 1) $LR=-Log(S/So)$ where S=concentration of viable organisms after specified contact time, and So=the initial concentration of viable organisms at time zero; and 2) $PK=(1-(S/So))\times100$. These values are shown below in Table 4.

TABLE 4

| Solution | Contact Time | Results Log Reduction (LR) | Percent Kill (PK) |
|---|---|---|---|
| Example 1 | 30 seconds | >7.05 | >99.999991 |

Neutralization control data revealed that the neutralizer was able to adequately neutralize this disinfectant. Observed counts were consistently higher than those expected. The test disinfectant solution of Example 1 had rapid and potent sporicidal activity. Specifically, the disinfectant solution of Example 1 was able to achieve greater than 7-log reduction within 30 seconds. As a control, the same culture was tested using the same concentration of peracetic acid with none of the other active ingredients (i.e. without the alcohol or silver content). The composition of Examples 1 exhibited a greater kill level by several orders of magnitude.

Example 9

Kill-Time Studies of Sporicidal Activity Using 2.4% Alkaline Glutaraldehyde Disinfectant For comparison purposes, a study was conducted to determine the antimicrobial activity of a 2.4% alkaline glutaraldehyde disinfectant on bacterial endospores from the test organism *Bacillus subtilis*. Glutaraldehyde disinfectant solution is a common disinfectant used in hospitals to kill bacteria and other pathogens that might otherwise be difficult to kill. This study was carried out by performing a standard kill-time suspension test using a suspension of *B. subtilis* endospores. A 15 minute contact time was evaluated.

A test suspension containing endospores from *Bacillus subtilis* (ATCC #19659) was prepared from a culture grown on Nutrient agar, to which additional sporulation enhancements were added. Plates were harvested with sterile water and endospores were purified by repeated centrifugations and resuspensions in water. The final wash was in 70 wt % ethanol for 30 minutes, to ensure the death of all vegetative bacteria. The spores were resuspended in water containing 0.1 wt % Tween 80 to prevent clumping and stored at 4° C. until used.

A neutralizer was prepared that consisted of 1 ml of freshly made, filter-sterilized sodium bisulfite solution at 5.28 wt %.

The "kill time" procedure was as follows: A 9.9 ml aliquot of the disinfectant was placed in a sterile glass culture tube. The tube was equilibrated in a 20° C. water bath. The tube of disinfectant, 9 ml of 2.4 wt % alkaline glutaraldehyde (Freshly activated CIDEXPLUS, 3.4%, Lot #:2002247TP—diluted to 2.4 wt % with sterile water), was inoculated with 100 µl of the test organism suspension at time zero. After 15 min, 1 ml of spore/disinfectant suspension was removed to 9 ml of neutralizer. The tube was mixed thoroughly. After 2 minutes, the neutralized suspension was serially diluted (1:1× 10, 1:1×10$^2$, 1:1×10$^3$, etc.) in physiological saline solution (PSS). The number of viable spores in selected dilution tubes was assayed by membrane filtration. One (1) ml aliquots were plated in duplicate. The membranes were washed with about 100 ml of sterile PSS and removed to Columbia agar plates. The plates were incubated at 37° C. for 20 hours. The number of colonies on each filter was counted and log reduction and percent kill values were computed.

As a control, a titer of the test suspension was computed by performing membrane filtration assays on selected 1:10 dilutions in PSS of the test suspension.

A neutralizer control was performed by inoculating a mixture of 1 ml of neutralizer and 1 ml of disinfectant with 100 µl of the 1:1×10$^5$ dilution of the titer. This produced about 450 CFU/ml in the tube, which was allowed to stand for 20 minutes prior to dilution and assay by membrane filtration using duplicate 1 ml samples.

The results are provided as follows:

TABLE 5a

| | Titer | | |
| --- | --- | --- | --- |
| | Dilution | | |
| | 1:1 × 10$^6$ | 1:1 × 10$^7$ | 1:1 × 10$^8$ |
| Number of Colonies | TNC* TNC | 96 93 | 0 0 |

TNC—Too Numerous to Count

TABLE 5b

Disinfectant solution (2.4 wt % alkaline glutaraldehyde disinfectant) Dilution of *B. subtilis* scores/disinfectant suspension

| | Dilution | | | |
| --- | --- | --- | --- | --- |
| | 1:1 × 10$^1$ | 1:1 × 10$^2$ | 1:1 × 10$^3$ | 1:1 × 10$^4$ |
| 15 minutes | TNC TNC | TNC TNC | TNC TNC | 259 52 |

TABLE 5C

| Neutralization control | | |
| --- | --- | --- |
| | Dilution | |
| | 1:1 × 10$^1$ | 1:1 × 10$^2$ |
| 15 Seconds | 72 70 | 1 4 |

Sterilization controls indicated zero growth for the glutaraldehyde, sodium bisulfite, water, PSS, and Columbia agar. Results of the titer showed a viable *B. subtilis* spore concentration of 9.45×10$^8$ spores per ml in the original suspension. Inoculation of 9.9 ml of disinfectant with 100 µl of this suspension produced an initial concentration of 9.45×10$^6$ spores per ml in the assay tube. Results from these procedures allowed log reduction (LR) and percent kill (PK) values to be calculated using the formulas: 1) LR=−Log(S/So) where S=concentration of viable organisms after 1 hour, and So=the initial concentration of viable organisms at time zero; and 2) PK=(1−(S/So))×100. These values are shown below in Table 6.

TABLE 6

| | Results | | |
| --- | --- | --- | --- |
| Solution | Contact Time | Log Reduction (LR) | Percent Kill (PK) |
| Alkaline glutaraldehyde | 15 min | 0.48 | 67.1 |

Neutralization control data revealed that the neutralizer was able to adequately neutralize this disinfectant. Observed counts were greater than those expected. The 2.4 wt % alkaline glutaraldehyde solution tested had relatively slow sporicidal activity, producing only a 0.48 log-reduction in 15 minutes, which is significantly lower than that produced by any of the exemplary compositions above prepared in accordance with embodiments of the present invention.

Example 10

Kill-Time Studies of *Mycobacterium bovis* Using Lysol® Spray

For comparison purposes, a study was conducted to determine tuberculocidal activity of a Lysol® spray disinfectant (Lysol Spray, spring waterfall scent Lot # B4194-NJ2 1413-A3) on a hard surface using the CRA Environmental Wipe Method. This method is fully described in: Christensen, R. P., R. A. Robison, D. F. Robinson, B. J. Ploeger, R. W. Leavitt, and H. L. bodily, Antimicrobial Activity of Environmental Surface Disinfectants in the Absence and Presence of Bioburden. Journal of the American Dental Association, 119:493-505. 1989.

Specifically, a test suspension containing *Mycobacterium bovis* (ATCC #35743) was prepared from a frozen suspension of a standardized culture grown in modified Proskauer-Beck medium. The suspension was thawed and mixed with an equal volume of phosphate-buffered gelatin solution in a Teflon-on-glass tissue grinder on ice. The suspension was homogenized for two minutes, then diluted 1:4 in physiological saline solution (PSS) containing 0.1% Tween 80. The suspension was vortexed and held on ice until used in inoculate the test surface.

A neutralizer mixture consisted of 50 ml flasks of Tryptic soy broth containing 1.0% Tween 80, 1.0% lecithin, and 50 µl of concentrated catalase solution (Sigma, C100, 42,300 units/mg).

The CRA environmental Wipe Method which was used is detailed below. An 8×12 inch piece of laminated plastic counter covering was secured to polypropylene dental trays (size B, Zirc Dental) with silicone adhesive. Lids and trays were sterilized by a hydrogen peroxide gas plasma sterilizer. Two ml of test organism suspension was applied to the surface with a sterile 2×2-in cotton-filled gauze sponge. The surface was allowed to dry 20-30 minutes in a biosafety cabinet under laminar flow. Then 3.5 ml of disinfectant (or water) was applied to a sterile gauze sponge, which was used to wipe the inoculated test surface for 10 seconds using about 150-g pressure with overlapping strokes (20 left to right, followed by 20 top to bottom). After 3 minutes, the trays were flooded with 50 ml of neutralizer and scrubbed for 1 minute with a sterile polypropylene brush to remove and suspend organisms. The fluid was collected and serially diluted 1:10 in physiological saline solution (PSS). The number of viable organisms in selected dilution tubes was assayed by membrane filtration. One ml aliquots were plated in duplicate. The membranes were washed with about 100 ml of sterile PSS and removed to Mycobacteria 7H11 agar plates. The plates were incubated at 37° C. for about three weeks. The number of colonies on each was counted and log reduction and percent kill values were computed.

As a control, a titer of the test suspension was computed by performing membrane filtration assays of selected 1:10 dilutions of the test suspension in PSS. A neutralizer control was performed by inoculating a mixture of 9 ml of neutralizer and 1 ml of disinfectant with 100 µl of the $1:10^3$ dilution of the titer containing 1750 CFU. This produced 175 CFU/ml in the tube, which was allowed to stand for 20 minutes prior to dilution and assay of the tubes by membrane filtration using duplicate 1 ml samples.

The results are provided as follows:

TABLE 7a

Titer

| | Dilution | | |
|---|---|---|---|
| | $1:1 \times 10^3$ | $1:1 \times 10^4$ | $1:1 \times 10^5$ |
| Number of Colonies | TNC* TNC | TNC TNC | 175 174 |

*TNC—Too Numerous to Count

TABLE 7b

Disinfectant solution (Lysol ® Spray)
Dilution of *M. bovis*/disinfectant suspension

| | | Dilution |
|---|---|---|
| | Undiluted | $1:1 \times 10^1$ |
| 3 minutes | TNC | 640 |
| | TNC | 486 |

TABLE 7c

Neutralization control
Undiluted 180
196

TABLE 7d

Sterility controls

| Material | Counts |
|---|---|
| Phosphate buffered gelatin | 0 |
| Neutralizer + catalas | 0 |
| Lysol Spray | 0 |
| Mycobacteria 7H11 Agar | 0 |
| Physiological sterile saline (PSS) + 0.1% Tween 80 | 0 |
| Physiological sterile saline (PSS) | 0 |

Results of the titer showed the initial concentration of *M. bovis* was 1.75×107 CFU per ml in the prepared suspension. Inoculation of the test surface following drying produced a challenge exhibited by the water control. The initial concentration of viable bacilli on the test surface (So) was $2.63 \times 10^5$. Results from these procedures allowed log reduction (LR) and percent kill (PK) values to be calculated using the formulas: 1) LR=−Log(S/So) where S=concentration of viable organisms after a period of exposure to the disinfectant; and So=the initial concentration of viable organisms at time zero; These values are shown in Table 8 below.

TABLE 8

Results

| Solution | Contact Time | Log Reduction (LR) | Percent Kill (PK) |
|---|---|---|---|
| Lysol ® Spray | 3 minutes | 0.97 | 89.3 |

The neutralization control data indicated that each test solution was adequately neutralized. Observed counts were similar to those expected from the titer data.

Example 11

Kill-Rate Enhancement Using Alloys

To demonstrate the effectiveness of certain alloys in enhancing the kill rate of B. Subtilis bacteria, a composition comprising 0.5% by weight of hydrogen peroxide, 8% by weight ethanol, and the balance of water containing 300 ppm of a colloidal silver was prepared. A similar composition was prepared using identical components except that aqueous solution contained a silver alloy admixture with manganese (approximately 300 ppm silver and about 7 ppm manganese). A kill test was performed resulting in a 0.13 log reduction or a 25.6% kill rate of the *B. subtilis* after 30 seconds using the colloidal silver composition. The kill study was also performed using the colloidal silver-manganese alloy composition, which resulted in a 0.24 log reduction or 42.6% kill after 30 seconds.

Example 12

Residual Kill Properties of a Disinfectant Solution

The disinfectant solution of Example 1 is prepared as described. The solution is applied to a Petri dish containing bacterial colonies. The bacterial colonies are killed. The disinfectant solution is allowed to remain in the Petri dish until the disinfectant solution appears to be visibly gone, i.e. after solvent evaporation. New active bacterial colonies are transplanted onto the Petri dish without adding additional disinfectant solution. Within a period of 24 hours, the transplanted colonies are likewise killed.

Example 13

Residual Kill Properties of a Disinfectant Solution

The same as Example 12 except that the disinfectant solution is not made using a two-part system, but rather using direct admixing of the ingredients.

Example 14

Two-Part Disinfectant Solution for Use with Wipes

A two-part solution of Example 2 is prepared in two compartments. The first compartment contains the first liquid composition and a stack of wipes. The second compartment contains the second liquid composition which is stable when compartmentalized. The first compartment is opened and the common wall between the first and second compartments is breached. The first liquid composition and the second liquid composition are admixed by re-closing the first container and gently shaking. Once the second liquid composition is thoroughly mixed with the first liquid composition, the peracetic acid concentration is significantly reduced, i.e. 1.3 wt %. The resultant disinfectant composition is now impregnated in the stack of wipes, and includes colloidal silver, glycerol, peracetic acid, and water.

Example 15

Two-Part Disinfectant Solution for Use with Wipes

The device is prepared as in Example 14, except a two part solution of Example 1, 3, 4, 5, or 6 is used.

Example 16

Two-Part Disinfectant Solution for Use as a Spray

A two-part solution of Example 2 is prepared in two compartments. The first compartment contains the first liquid composition, and the second compartment contains the second liquid composition which is stable when compartmentalized. Both compartments include a nozzle opening, each of which is used to transfer its liquid therethough to a mixing chamber. Once the second liquid composition is thoroughly mixed with the first liquid composition, the peracetic acid concentration is significantly reduced, i.e. 1.3 wt %. Upon mixing, a resultant disinfectant solution is sprayable onto a surface.

Example 17

Two-Part Disinfectant Solution for Use as a Spray

The device is prepared as in Example 16, except a two part solution of Example 1, 3, 4, 5, or 6 is used.

While the invention has been described with reference to certain preferred embodiments, those skilled in the art will appreciate that various modifications, changes, omissions, and substitutions can be made without departing from the spirit of the invention. It is therefore intended that the invention be limited only by the scope of the appended claims.

What is claimed is:

1. A method for formulating a disinfecgtant solution comprising contacting two liquid compositions in a dispensing device, said device comprising:

a first compartment containing a first liquid composition comprising a colloidal transition metal, wherein the colloidal transition metal is an elemental metal selected from the group consisting of ruthenium, rhodium, osmium, iridium, palladium, platinum, copper, gold, silver, manganese, zinc, alloys thereof, and mixtures thereof; and a second compartment, separated from the first compartment, containing a second liquid composition comprising a peroxygen, said liquids forming a disinfectant solution when brought together.

2. The method of claim 1, further comprising a third compartment separated from the first compartment and the second compartment.

3. The method of claim 1, wherein either the first compartment or the second compartment is substantially encompassed by the other compartment.

4. The method of claim 1, wherein the first compartment and the second compartment share a common wall.

5. The method of claim 4, wherein the common wall is frangible.

6. The method of claim 1, wherein a portion of the first compartment or a portion of the second compartment is removable or modifiable.

7. The method of claim 6, wherein the portion is removable.

8. The method of claim 7, wherein the portion is replaceable.

9. The method of claim 6, wherein the portion is modifiable.

10. The method of claim 9, wherein the portion is configured to be punctured.

11. The method of claim 1, wherein the first liquid composition is present in the first compartment and the second liquid composition is present in the second compartment in a volume ratio from about 10:1 to about 1:10.

12. The method of claim 1, wherein the first liquid composition is present in the first compartment and the second liquid composition is present in the second compartment in a volume ratio from about 5:1 to about 1:5.

13. The method of claim 1, wherein the first liquid composition is present in the first compartment and the second liquid composition is present in the second compartment in a volume ratio from about 2:1 to about 1:2.

14. The method of claim 1, wherein the first liquid composition is present in the first compartment and the second liquid composition is present in the second compartment in a single dose amount.

15. The method of claim 1, further comprising wipes.

16. The method of claim 15, wherein the wipes are in a third compartment.

17. The method of claim 15, wherein the wipes are dry.

18. The method of claim 15, wherein the wipes are in the first compartment or in the second compartment.

19. The method of claim 15, wherein the wipes are prewetted with either the first liquid composition or the second liquid composition.

20. The method of claim 19, wherein the wipes are prewetted with an accelerating agent.

21. The method of claim 1, wherein the first compartment or the second compartment comprises a polymer material.

22. The method of claim 1, further comprising a nozzle fluidly coupled to at least one of the first compartment, the second compartment, and optionally further comprising a third compartment, configured for receiving a hose attachment.

23. The method of claim 22, further comprising at least one hose connected to at least one of the first compartment, the second compartment, and the third compartment.

24. The method of claim 22, wherein the hose is configured for variable spray patterns or dispensing flow rates.

25. The method of claim 1, wherein the dispensing device is configured to generate a foam.

26. The method of claim 1, further comprising a gelling agent configured to contact the first liquid composition, the second liquid, or a mixture of the first liquid composition and second liquid composition.

27. The method of claim 1, wherein the first compartment and the second compartment are encompassed by an outer shell.

28. The method of claim 1, wherein the device is substantially flexible.

29. The method of claim 1, further comprising a pump associated with at least one of the first compartment and the second compartment for pumping liquid from one location to another.

30. The method of claim 29, wherein the pump is configured for manual operation.

31. The method of claim 29, wherein the pump is configured for automatic operation.

32. The method of claim 29, wherein the pump is configured to eject disinfectant from the dispensing device.

33. The method of claim 29, wherein the pump is configured to eject liquid into the first compartment or the second compartment, or optionally further comprising a third compartment.

34. The method of claim 29, wherein the pump is configured to dispense a single dose.

35. The method of claim 1, wherein the disinfectant solution has greater kill potency for pathogens compared to the first liquid composition and the second liquid composition when either is used alone.

36. The method of claim 1, wherein at least one of the first liquid composition and the second liquid composition further comprises water.

37. The method of claim 1, wherein at least one of the first liquid composition and the second liquid composition further comprises alcohol.

38. The method of claim 37, wherein the alcohol is present in the first compartment.

39. The method of claim 37, wherein the alcohol is present in the first liquid composition or the second liquid composition a concentration of from about 0.05 wt % to about 80 wt %.

40. The method of claim 37, wherein the alcohol is a $C_1$-$C_{24}$ alcohol.

41. The method of claim 1, wherein the colloidal transition metal or alloy thereof has an average particle size of from 0.001 µm to 1.0 µm.

42. The method of claim 1, wherein the transition metal or alloy thereof is present in the first liquid composition at from 0.01 ppm to 20,000 ppm by weight.

43. The method of claim 1, wherein the peroxygen is present in the second liquid composition at greater than 14 wt %.

44. The method of claim 1, wherein the peroxygen is present in the disinfectant solution at from 0.1 wt % to 10 wt %.

45. The method of claim 1, wherein the peroxygen is present in the disinfectant solution at from 0.2 wt % to 5 wt %.

46. The method of claim 1, wherein the peroxygen is present in the disinfectant solution at from 0.3 wt % to 2 wt %.

47. A system for dispensing a disinfectant solution, comprising:
a first compartment containing a first liquid composition, said first liquid composition including a colloidal transition metal, wherein the colloidal transition metal is an elemental metal selected from the group consisting of ruthenium, rhodium, osmium, iridium, palladium, platinum, copper, gold, silver, manganese, zinc, alloys thereof, and mixtures thereof;
a second compartment containing a second liquid composition, said second liquid composition including a peroxygen; and
a separator between the first and the second compartments which can be modified or removed to cause the first liquid composition and the second liquid composition to contact one another to form the disinfectant solution.

48. The system of claim 47, wherein the separator is a common wall.

49. The system of claim 48, wherein the common wall is frangible.

50. The system of claim 48, wherein the common wall is configured to open when a safety device is opened or breached.

51. The system of claim 47, further comprising wipes in the first compartment or the second compartment.

52. The system of claim 51, wherein the wipes are premoistened.

53. The system of claim 51, wherein the wipes are pre-moistened with a portion of the first liquid composition or the second liquid composition.

54. The system of claim 51, wherein the wipes are dry.

55. The system of claim 47, further comprising a third compartment.

56. The system of claim 55, further comprising wipes in the third compartment.

57. The system of claim 51, wherein the wipes are pre-moistened.

58. The system of claim 51, wherein the wipes are dry.

59. The system of claim 47, wherein the first compartment is enclosed in the second compartment or the second compartment is enclosed in the first compartment.

60. The system of claim 47, wherein the separator is optionally replaceable.

61. The system of claim 47, wherein the first and second liquid compositions together have greater kill potency for pathogens compared to the first liquid composition or the second liquid composition used individually.

62. The system of claim 47, wherein at least one of the first liquid composition and the second liquid composition further comprises water.

63. The system of claim 47, wherein at least one of the first liquid composition and the second liquid composition further comprises alcohol.

64. The system of claim 63, wherein the alcohol is present in the first liquid composition.

65. The system of claim 47, wherein the peroxygen is present in the second liquid composition at from about 14 wt % to about 99 wt %.

66. A device, comprising multiple systems of claim 47 in the form of multiple pods, each pod providing an independent single dose of the disinfectant solution when the first liquid composition and the second liquid composition is mixed within that system.

67. A method of disinfecting a surface, comprising:
providing a first compartment containing a first liquid composition comprising a colloidal transition metal, wherein the colloidal transition metal is an elemental metal selected from the group consisting of ruthenium, rhodium, osmium, iridium, palladium, platinum, copper, gold, silver, manganese, zinc, alloys thereof, and mixtures thereof;
providing a second compartment, separated from the first compartment, containing a second liquid composition comprising a peroxygen;
bringing together the first liquid composition and the second liquid composition to form a disinfectant solution within a device which comprises the first compartment and the second compartment; and
applying the disinfectant solution to the surface.

68. The method of claim 67, wherein the device further comprises a third compartment separated from the first compartment and the second compartment, said third compartment containing a third liquid composition which is also brought together with the first and second liquid compositions within the device to become part of the disinfectant solution.

69. The method of claim 67, wherein the first compartment and the second compartment share a common wall within the device, said common wall being configured to allow a user to cause the bringing together of the first liquid composition and the second liquid composition.

70. The method of claim 69, wherein at least a portion of the common wall is frangible.

71. The method of claim 69, wherein at least a portion of the common wall removable.

72. The method of claim 69, wherein at least a portion of the common wall is configured to be punctured.

73. The method of claim 67, wherein the first liquid composition is present in the first compartment and the second liquid composition is present in the second compartment in a volume ratio from about 10:1 to about 1:10.

74. The method of claim 67, wherein the first liquid composition is present in the first compartment and the second liquid composition is present in the second compartment so that the disinfectant solution is formed as a single dose amount.

75. The method of claim 67, further comprising the step of causing the disinfectant solution to become absorbed, impregnated, or coated onto at least one wipe.

76. The method of claim 75, wherein the at least one wipe is pre-moistened.

77. The method of claim 75, wherein the at least one wipe is dry.

78. The method of claim 67, further comprising the step of causing the first liquid composition and the second composition to come together to form the disinfectant solution in a third compartment.

79. The method of claim 78, wherein the third compartment is present within a dispensing device that is hooked to nozzles present on the first compartment and the second compartment.

80. The method of claim 67, wherein the device is configured to generate a gelled, foamed, or aerosolized disinfectant solution.

81. The method of claim 67, wherein the disinfectant solution has greater kill potency for pathogens compared to the first liquid composition and the second liquid composition when either is used alone.

82. The method of claim 67, wherein at least one of the first liquid composition and the second liquid composition further comprises alcohol.

83. The method of claim 82, wherein the alcohol is a $C_1$-$C_{24}$ alcohol.

84. The method of claim 82, wherein the alcohol is a polyhydric alcohol.

85. The method of claim 67 wherein the colloidal transition metal or alloy thereof has an average particle size of from 0.001 μm to 1.0 μm.

86. The method of claim 67, wherein the transition metal or alloy thereof is present in the first liquid composition at from 0.01 ppm to 20,000 ppm by weight.

87. The method of claim 67, wherein the transition metal or alloy thereof is colloidal silver.

88. The method of claim 67, wherein the peroxygen includes a peracid.

89. The method of claim 67, wherein the peroxygen is present in the second liquid composition at greater than 14 wt %.

90. The method of claim 67, wherein the peroxygen is present in the disinfectant solution at from 0.1 wt % to 10 wt %.

91. The method of claim 67, wherein the peroxygen is present in the disinfectant solution at from 0.2 wt % to 5 wt %.

92. A method for formulating a disinfectant solution comprising contacting two liquid compositions in a dispensing device, said device comprising:
a first compartment containing a first liquid composition comprising a colloidal transition metal, wherein the colloidal transition metal is an elemental metal selected from the group consisting of ruthenium, rhodium, osmium, iridium, palladium, platinum, copper, gold, silver, manganese, zinc, alloys thereof, and mixtures thereof; and a second compartment, separated from the first compartment, containing a second liquid composition comprising a peroxygen;

wherein at least one of said first liquid composition or said liquid composition includes polyhydric alcohol, said liquids forming a disinfectant solution when brought together. metal, wherein the colloidal transition metal is an elemental metal selected from the

93. A method for formulating a disinfectant solution comprising contacting two liquid compositions in a dispensing device, said device comprising:

a first compartment containing a first liquid composition comprising a colloidal transition metal, wherein the colloidal transition metal is an elemental colloidal silver; and a second compartment, separated from the first compartment, containing a second liquid composition comprising a peroxygen, said liquids forming a disinfectant solution when brought together.

94. A method for formulating a disinfectant solution comprising contacting two liquid compositions in a dispensing device, said device comprising:

a first compartment containing a first liquid composition comprising a colloidal transition metal, wherein the colloidal transistion metal is an elemental metal selected from the group consisting of ruthenium, rhodium, osmium, iridium, palladium, platinum, copper, gold, silver, manganese, zinc, alloys thereof, and mixtures thereof; and a second compartment, separated from the first compartment, containing a second liquid composition comprising a peroxygen, said peroxygen including a peracid, said liquids forming a disinfectant solution when brought together.

* * * * *